United States Patent [19]
Chadwick et al.

[11] Patent Number: 5,329,038
[45] Date of Patent: Jul. 12, 1994

[54] PROCESS FOR HYDROGENATION OF CHLOROSILANE

[75] Inventors: Kirk M. Chadwick, Barry, United Kingdom; Roland L. Halm, Madison, Ind.; Brian R. Keyes, Corpus Christi, Tex.

[73] Assignee: Dow Corning Corporation, Midland, Mich.

[21] Appl. No.: 175,324

[22] Filed: Dec. 29, 1993

[51] Int. Cl.$^5$ .................................................. C07F 7/08
[52] U.S. Cl. .................................... 556/474; 423/342; 423/347
[58] Field of Search ................. 556/474; 423/342, 347

[56] References Cited

U.S. PATENT DOCUMENTS

| | | | |
|---|---|---|---|
| 2,406,605 | 8/1946 | Hurd | 556/474 |
| 2,458,703 | 1/1949 | Hatcher | 556/474 |
| 2,595,620 | 5/1952 | Wagner et al. | 556/474 |
| 3,057,686 | 10/1962 | Muetterties | 556/474 |
| 3,100,788 | 8/1963 | Jenkner | 556/474 |
| 3,439,008 | 4/1969 | Berger | 556/474 |
| 3,496,206 | 2/1970 | Berger | 556/474 |
| 3,657,302 | 4/1972 | Duffaut et al. | 556/474 |
| 4,542,005 | 9/1985 | Tetsuya et al. | 423/347 |
| 4,810,482 | 3/1989 | Iwao et al. | 423/347 |
| 4,925,963 | 5/1990 | Marlett | 556/474 |
| 5,015,624 | 5/1991 | Schulz | 556/474 |

OTHER PUBLICATIONS

Kirk & Othmer, Encyclopedia of Chemical Technology; The Interscience Group, New York, N.Y., vol. 12, p. 368, 1978.

*Primary Examiner*—Paul F. Shaver
*Attorney, Agent, or Firm*—William F. Boley

[57] ABSTRACT

A process for the hydrogenation of chlorosilanes. The process comprises contacting a chlorosilane with aluminum and a hydrogen source selected from a group consisting of hydrogen gas and gaseous hydrogen chloride in the presence of a catalyst. The catalyst is selected from a group consisting of copper and copper compounds, tin and tin compounds, zinc and zinc compounds, and mixtures thereof.

22 Claims, No Drawings

PROCESS FOR HYDROGENATION OF CHLOROSILANE

BACKGROUND OF INVENTION

The present invention is a process for the hydrogenation of chlorosilanes. The process comprises contacting a chlorosilane with aluminum and a hydrogen source selected from a group consisting of hydrogen gas and gaseous hydrogen chloride in the presence of a catalyst. The catalyst is selected from a group consisting of copper and copper compounds, tin and tin compounds, zinc and zinc compounds, and mixtures thereof.

Industrially significant methods for producing hydrosilanes involve, for example, the reaction of a halosilane with a metal hydride in the presence of a solvent as described in Kirk and Othmer, Encyclopedia of Chemical Technology; The Interscience Group, New York, N.Y, Vol. 12, p. 368, 1978. The preferred metal hydride reagents are LiAlH$_4$ and NaAlH$_4$. The reaction is reported to proceed quantatively at low system pressure and temperature. However, metal hydride reagents offer significant processing disadvantages. First, they are highly reactive and may oxidize exothermically to release explosive concentrations of hydrogen gas. Because of this, hydrogenation reactions with these reagents are typically carried out in solvents. The use of solvents presents a second disadvantage in that the solvent must be separated from the product. If solvents are not used, the metal may be stabilized by replacing a portion of the metal hydride ligands with bulky organic substituents. While this eliminates the solvent, it necessarily reduces the equivalent hydrogenation potential for the metal hydrides.

Non-metal hydride, non-solvent systems for hydrogenating halosilanes have also been reported. Hurd, U.S. Pat. No. 2,406,605, issued Aug. 27, 1946, disclosed the reaction of certain halosilanes with hydrogen or a hydrogen halide at an elevated temperature with a metal selected from a group consisting of aluminum, magnesium, and zinc. At temperatures of 400° C. to 500° C. and atmospheric pressure, Hurd determined that SiCl$_4$ and MeSiCl$_3$ could be reacted to SiHCl$_3$ and MeHSiCl$_2$ respectively. Hurd reported that the reaction of Me$_2$SiCl$_2$ was generally unsuccessful, even at 500° C.

Hatcher, U.S. Pat. No. 2,458,703, issued Jan. 11, 1949, reported a method of hydrogenating halosilanes using silicon as a chloride acceptor in a continuous high-pressure system. Hatcher reported that the silicon could reduce a halosilane in a hydrogen atmosphere when AlCl$_3$ or AlBr$_3$ was present.

Wagner et al., U.S. Pat. No. 2,595,620, issued May 6, 1952, reported that silicon could be used to reduce a chlorosilane with hydrogen at temperatures above about 400° C. and the AlCl$_2$ or AlBr$_3$ required by Hatcher, supra, was not necessary.

Muetterties, U.S. Pat. No. 3,057,686, issued Oct. 9, 1962, reported a hydrogenation process where a halosilane was reacted with hydrogen and activated aluminum metal at superatmospheric pressure. Muetterties described the activated aluminum as a metal having an essentially oxygen free surface. The groups of compositions suitable for activating the aluminum as described by Muetterties were (1) metal hydrides, (2) mixtures of iodine and an alkyl halide in which the halogen has an atomic number of at least 17, and (3) trialkyl aluminum compounds.

Jenkner, U.S. Pat. No. 3,100,788, issued Aug. 13, 1963, reported a process for hydrogenation of halosilanes with hydrogen gas using sodium metal as the halogen receptor.

The present invention is a process for the hydrogenation of chlorosilane by a hydrogen source selected from a group consisting of hydrogen gas and gaseous hydrogen chloride. The process uses aluminum as the halogen receptor. The process does not require a solvent and can be run at near atmospheric pressure. The process employs a catalyst selected from a group consisting of copper and copper compounds, tin and tin compounds, zinc and zinc compounds, and mixtures thereof. Under the described process conditions, the catalyst provides for increased formation of silicon hydrogen bonds and increased chlorosilane conversion, when compared to the use of aluminum without catalyst. The catalyst also allows the process to be run at a lower temperature than that used for similar uncatalyzed processes.

Hydrosilanes prepared by the present process are useful intermediates in the formation, for example, of silicone polymers, elastomers, and resins.

SUMMARY OF INVENTION

The present invention is a process for the hydrogenation of chlorosilanes. The process comprises contacting a chlorosilane with aluminum and a hydrogen source selected from a group consisting of hydrogen gas and gaseous hydrogen chloride in the presence of a catalyst. The catalyst is selected from a group consisting of copper and copper compounds, tin and tin compounds, zinc and zinc compounds, and mixtures thereof.

DESCRIPTION OF INVENTION

The present invention is a process for the hydrogenation of chlorosilanes. The process comprises contacting a chlorosilane described by formula $$R_aH_bSiCl_{4-a-b} \tag{1}$$

where each R is independently selected from a group consisting of alkyls comprising one to six carbon atoms, a=0, 1, 2, or 3; b=0, 1, 2, or 3; and a+b=0, 1, 2, or 3; with aluminum and a hydrogen source selected from a group consisting of hydrogen gas and gaseous hydrogen chloride, in the presence of a catalyst selected from a group consisting of copper and copper compounds, tin and tin compounds, zinc and zinc compounds, and mixtures thereof, and recovering a hydrosilane resulting from the exchange of one or more of the chlorine atoms of the chlorosilane by hydrogen.

Contacting the chlorosilane with aluminum, hydrogen source, and catalyst can be effected in standard reactors for contacting chlorosilanes and solids. The reactor can be, for example, a fixed-bed reactor, a stirred-bed reactor, or a fluidized-bed reactor. The present process can be run as a batch process, semi-continuous, or continuous process. Since the aluminum trichloride produced in the present process can act as a redistribution catalyst for alkyls and hydrogen substituted on silicon, it is generally preferred that the process be run as a continuous process to allow rapid separation of the aluminum trichloride from the hydrogenated chlorosilanes.

Chlorosilanes which can be hydrogenated in the present process are described by formula (1). In formula (1) each R is independently selected from a group consisting of alkyls comprising one to six carbon atoms. The alkyl can be, for example, methyl, ethyl, propyl, isopropyl, n-butyl, tert-butyl, and hexyl. Preferred is when R is methyl. Chlorosilanes which can be hydrogenated by the present invention include, for example, tetrachlorosilane, methyltrichlorosilane, dimethyldichlorosilane, and trimethylchlorosilane. The present process is especially useful for hydrogenating dimethyldichlorosilane to dimethylchlorosilane.

The present process employs aluminum as a chlorine receptor, forming aluminum chloride as a by-product. The aluminum can be added to the process, for example, as a powder, particulate, flakes, shot, or wire. Typically, the present process is run using a fixed-bed or fluidized-bed of aluminum. Therefore, the process is run using a large excess of aluminum in relation to that required as a chlorine receptor.

The present process uses a catalyst selected from a group consisting of copper and copper compounds, tin and tin compounds, zinc and zinc compounds, and mixtures thereof. The catalyst can be of the same physical forms as described for the aluminum. It is preferred, but not necessary, that the catalyst be mixed with the aluminum to form a relative homogeneous mixture. Mixing can be accomplished by standard means for mixing powders, for example, mechanical stirring or by shaking.

The catalyst can be copper metal, copper compound, or a mixture thereof. The copper compound can be an inorganic or organic compound of copper. The inorganic copper compound can be, for example, a copper halide or copper oxide. A preferred inorganic copper compound is copper formate.

The copper metal, copper compound, or a mixture thereof is added to the process so as to provide a concentration of copper of about 0.1 to 20 weight percent in relation to the aluminum.

The catalyst can be tin metal, tin compound, or a mixture thereof. The catalyst can be an inorganic or organic tin compound. The inorganic tin compound can be, for example, tin halide or tin hydride. The inorganic tin compound can be, for example, tin chloride. The catalyst can be an organic tin compound such as trimethyltin.

The weight of tin, tin compound, or mixture thereof used as catalyst in the present process can be that which provides about 1500 ppm to 10,000 ppm tin in relation to the weight of the aluminum. Preferred is when the weight of tin provided to the process as catalyst is within a range of about 3,000 ppm to 5,000 ppm.

The catalyst can be zinc metal, a zinc compound, or a mixture thereof. The catalyst can be an inorganic zinc compound or an organic zinc compound. The inorganic zinc compound can be, for example, a zinc halide or zinc hydride. The organic zinc compound can be, for example, dimethyzinc All or a portion of the zinc may be provided to the process by brass.

The weight of zinc, zinc compound, or mixture thereof used as catalyst in the present process can be that which provides about 100 ppm to 10,000 ppm zinc in relation to the weight of the aluminum.

The catalyst can be a mixture comprising of one or more of copper metal, copper compounds, tin metal, tin compounds, zinc metal, and zinc compounds. A preferred catalyst for the present process is a mixture comprising CuCl, tin metal, and zinc metal. It is desirable that this mixture be added to the process to provide a final concentration with the aluminum of about 0.1 to 20 percent CuCl, 5 to 2000 ppm tin, and 100 to 10,000 ppm zinc. All or a portion of the zinc in the catalyst mixture may be provided by brass. A preferred catalyst mixture provides in mixture with the aluminum about 10-15 weight percent CuCl, 1500-2000 ppm tin, and 3500-4200 ppm brass.

The present process employs a hydrogen source to reduce the chlorosilane. The hydrogen source is selected from a group consisting of hydrogen gas and gaseous hydrogen chloride. For optimal results, it is preferred that the mole ratio of hydrogen source provide at least one mole of hydrogen per mole of chlorosilane. A lessor mole ratio of hydrogen to chlorosilane may be used, but may result in reduced process yield. It is preferred that the mole ratio of hydrogen to chlorosilane (H:Si) be within a range of about one to four. Generally, increasing the mole ratio of hydrogen increases the average number of hydrogens atoms bonded to the silicon of the chlorosilane.

The present process can be run at a reactor pressure of about one atmosphere (atm) to about 100 atm. It is preferred that the process be run at a reactor pressure within a range of about one atm. to fifteen atm.

Residence time of the chlorosilane within the reactor general requires a balancing between allowing sufficient time for hydrogenation to occur without excessive redistribution of silicon bonded alkyl substituents. Generally a residence time of about 0.1 second to 5 minutes is considered useful. Preferred is a residence time of about one second to one minute.

The preferred temperature for running the present process will depend upon the chlorosilane and the hydrogen source fed to the process. Generally, as the temperature is increased the conversion of feed chlorosilanes to other species increases, but the redistribution reaction of silicon-bonded alkyls also increases. When the hydrogen source is hydrogen gas, a useful temperature range is considered to be within a range of about 300° C to 450° C. When the hydrogen source is hydrogen gas, a preferred temperature is within a range of about 325° C to 375° C. When the hydrogen source is gaseous hydrogen chloride, a useful temperature is considered to be within a range of about 250° C. to 450° C. When the hydrogen source is gaseous hydrogen chloride, a preferred temperature is within a range of about 270° C. to 350° C.

The inventors have found that the present process is more consistent in product distribution and yield when the mixture comprising the aluminum and catalyst is preheated prior to contact with the chlorosilane and hydrogen source. Therefore, in a preferred embodiment the mixture comprising aluminum and the catalyst is preheated. Preheating can be conducted at any temperature within the temperature ranges provided for conduct of the process. The length of time of preheating will depend both upon the efficiency of heating and should be determined for each specific reactor configuration. For example using a reactor such as described in the present examples, an optimal heating time was found to be within a range of about eight to 13 minutes. However, preheating times of 0.5 minute to 45 minutes were found to be useful.

In the present process one or more of the chlorine atoms substituted on the silicon atoms of the chlorosilane is replaced with hydrogen forming a hydrosilane product. The hydrosilane product can be, for example, dimethylsilane, dimethylchlorosilane, methyldichlorosilane, and trimethylsilane. A preferred hydrosilane product is selected from a group consisting of dimethylchlorosilane and trimethylsilane.

The following examples are provided to illustrate the present invention. These examples are not intended to limit the scope of the present claims.

EXAMPLE 1

(Control) The hydrogenation of dimethyldichlorosilane by hydrogen gas in the presence of aluminum, with no catalyst, was evaluated. The process was conducted in a one-inch carbon-steel reactor which was immersed in a fluidized-sand temperature bath. The input end of the reactor was connected to a stainless steel vaporization coil which was also immersed in the temperature bath and which served to vaporize the dimethyldichlorosilane. The exit end of the reactor was connected to a series of two flask serving as collection traps. The first trap was maintained at a temperature of about 100° C. to trap aluminum trichloride exiting the reactor. The second trap was immersed in dry ice and served to collect the chlorosilanes exiting the reactor.

The reactor was charged with about 90 g of powdered aluminum (Alcan 44, Alcan-Toyo American, Joliet, IL). The reactor was purged with nitrogen gas and placed into the temperature bath maintained at a temperature of about 365° C. The reactor was allowed to set in the temperature bath for about 12 minutes as a preheat treatment. Then, hydrogen gas and dimethyldichlorosilane were fed to the reactor at a molar ratio of hydrogen to chlorosilane (H:Si) of 2.3 with a residence time in the reactor of about 11 seconds. Pressure in the reactor was about one atm. Feed to the reactor was continued for five hours, with gases exiting the reactor being collected in the described traps. The collected chlorosilane was analyzed by gas chromatography (GC) using a thermoconductivity detector (TC). A mass spectrometer (MS) was periodically used to confirm composition. The results are reported in Table 1. The heading "%Si Conv." represents the percent conversion of the dimethyldichlorosilane to other species.

TABLE 1

Reaction of Dimethyldichlorosilane With Hydrogen Gas and Aluminum in The Absence of Catalyst

| % Si Conv. | Weight Percent Product Distribution | | | | | | | |
|---|---|---|---|---|---|---|---|---|
| | $Me_2H_2$ | $Me_2H$ | MeH | $Me_3H$ | Me | $Me_2$ | $Me_3$ | $Me_4$ |
| 0.4 | 0.0 | 68.0 | 15.2 | 0.0 | 0.0 | 0.0 | 16.8 | 0.0 |

In Table 1, $Me_2H_2 = Me_2SiH_2$, $Me_2H = Me_2HSiCl_2$, $MeH = MeHSiCl_2$, $Me_3H = Me_3SiH$, $Me = MeSiCl_3$, $Me_2 = Me_2SiCl_2$, $Me_3 = Me_3SiCl$, and $Me_4 = Me_4Si$.

EXAMPLE 2

A series of runs was conducted to evaluate the variability of the process when no preheating of a mixture of tin catalyst and aluminum is used prior to contacting with a mixture of dimethyldichlorosilane and hydrogen gas. The runs were conducted in a reactor similar to that described in Example 1. Powdered tin (Belmont Metals Inc., Brooklyn, NY) was mixed with about 90 g of aluminum (as previously described) at a concentration of about 4000 ppm. This mixture was added to the reactor and the reactor purged with nitrogen. The reactor was immersed in a temperature bath at about 365° C and the feed of dimethyldichlorosilane and hydrogen gas immediately started to the reactor. The molar ratio of hydrogen to dimethyldichlorosilane was within a range of about 2.9 to 3.2. Residence time of the reactants within the reactor was about 12 to 13 seconds. All runs were conducted at a reactor pressure of about one atm. Products from each run were collected and analyzed as described in Example 1. The results are reported in Table 2.

TABLE 2

Tin Catalyzed Reaction of Dimethyldichlorosilane With Hydrogen Gas and Aluminum - No Preheat Treatment

| Run No. | % Si Conv. | Weight Percent Product Distribution | | | | | | | |
|---|---|---|---|---|---|---|---|---|---|
| | | $Me_2H_2$ | $Me_2H$ | MeH | $Me_3H$ | Me | $Me_2$ | $Me_3$ | $Me_4$ |
| 137 | 8.0 | 0.5 | 16.4 | 0.6 | 0.0 | 1.0 | 0.0 | 80.2 | 1.2 |
| 140 | 50.6 | 1.0 | 10.7 | 0.1 | 0.7 | 0.0 | 0.0 | 84.4 | 3.1 |
| 141 | 59.1 | 0.2 | 8.5 | 0.3 | 0.6 | 0.0 | 0.0 | 87.6 | 2.8 |

For the data provided in Table 2 the average value for % Si Conv. is 39.2.

EXAMPLE 3

A series of runs was conducted to evaluate the variability of the process when a mixture of aluminum and tin is subject to a preheat treatment prior to contact with a dimethyldichlorosilane and hydrogen gas mixture. The runs were conducted in a reactor similar to that described in Example 1. A mixture of tin and aluminum as described in Example 2 was formed and added to the reactor. The reactor was purged with nitrogen, placed in a 365° C. temperature bath for eight to 13 minutes, and then feed of a mixture of dimethyldichlorosilane and hydrogen gas was started. The molar ratio of hydrogen to dimethyldichlorosilane was within a range of about 3.1 to 3.4. Residence time of the reactants within the reactor was about 12 to 13 seconds. For all runs, the pressure in the reactor was about one atm. Products from each run were collected and analyzed as described in Example 1. The results are reported in Table 3.

TABLE 3

Tin Catalyzed Reaction of Dimethyldichlorosilane With Hydrogen Gas and Aluminum - Effects of Heat Pretreatment

| Run No. | % Si Conv. | Weight Percent Product Distribution | | | | | | | |
|---|---|---|---|---|---|---|---|---|---|
| | | $Me_2H_2$ | $Me_2H$ | MeH | $Me_3H$ | Me | $Me_2$ | $Me_3$ | $Me_4$ |
| 144 | 59.4 | 1.0 | 7.3 | 0.3 | 3.1 | 0.2 | 0.0 | 84.2 | 4.0 |
| 145 | 66.2 | 0.6 | 5.8 | 0.3 | 0.4 | 0.2 | 0.0 | 90.0 | 2.8 |
| 148 | 42.1 | 0.1 | 11.3 | 0.8 | 0.4 | 0.1 | 0.0 | 86.8 | 0.6 |
| 149 | 82.0 | 0.4 | 4.9 | 0.2 | 1.6 | 1.5 | 0.0 | 88.8 | 2.5 |

For the data provided in Table 3, the average value for Si Conv. is 62.5.

EXAMPLE 4

The ability of tin to catalyze the reaction of dimethyldichlorosilane with hydrogen gas and aluminum was evaluated at a temperature of 325° C. Two runs were made in a reactor similar to that described in Example 1. A mixture of aluminum and tin as described in Example 2 was formed and added to the reactor. The reactor was purged with nitrogen and placed in a 325° C. temperature bath for about 10 minutes before start of the dimethyldichlorosilane and hydrogen gas feed. The molar ratio of hydrogen to dimethyldichlorosilane was about 3.0 to 3.1. Residence time of the reactants within the reactor was about 5.3 to 5.8 seconds. Pressure in the reactor was about one atm. Products from each run were collected and analyzed as described in Example 1. The results are reported in Table 4.

TABLE 4

| | Tin Catalyzed Reaction of Dimethyldichlorosilane With Hydrogen Gas and Aluminum at 325° C. | | | | | | | |
|---|---|---|---|---|---|---|---|---|
| | | Weight Percent Product Distribution | | | | | | |
| Run No. | % Si Conv. | $Me_2H_2$ | $Me_2H$ | MeH | $Me_3H$ | Me | $Me_2$ | $Me_3$ | $Me_4$ |
| 242 | 1.3 | 0.0 | 12.8 | 0.0 | 2.2 | 0.0 | 0.0 | 73.0 | 12.1 |
| 243 | 1.1 | 0.0 | 16.2 | 0.0 | 0.9 | 0.0 | 0.0 | 68.6 | 14.3 |

EXAMPLE 5

The tin catalyzed reaction of methyltrichlorosilane with hydrogen gas and aluminum was evaluated at one atmosphere of pressure and at four atmosphere of pressure. The runs were conducted in a reactor similar to that described in Example 1. Mixtures of tin and aluminum as described in Example 2 were formed and added to the reactor. The reactor was purged with nitrogen and pre-heated in a 365° C. temperature bath for 11 to 12 minutes prior to start of a methyltrichlorosilane and hydrogen gas feed to the reactor. For run number 156 the pressure within the reactor was one atm. The molar ratio of hydrogen to methyltrichlorosilane was 1.15 and the residence time of the reactants within the reactor was about 10.4 seconds. For run number 153 the pressure in the reactor was four atmosphere. The molar ratio of hydrogen to methyltrichlorosilane was 2.9 and the residence time of the reactants within the reactor was about 52.2 seconds. Products from the reactor were collected and analyzed as described in Example 1. The results are reported in Table 5.

TABLE 5

| | Tin Catalyzed Reaction of Methyltrichlorosilane With Hydrogen Gas and Aluminum | | | | | | | |
|---|---|---|---|---|---|---|---|---|
| | | Weight Percent Product Distribution | | | | | | |
| Run No. | % Si Conv. | $Me_2H_2$ | $Me_2H$ | MeH | $Me_3H$ | Me | $Me_2$ | $Me_3$ | $Me_4$ |
| 156 | 0.1 | 0.0 | 4.0 | 50.0 | 0.0 | 0.0 | 0.0 | 40.0 | 4.0 |
| 153 | 4.4 | 0.3 | 0.9 | 30.4 | 0.0 | 0.0 | 52.6 | 15.9 | 0.0 |

EXAMPLE 6

The tin catalyzed reaction of trimethylchlorosilane with hydrogen gas and aluminum was evaluated. The run was conducted in a reactor similar to that described in Example 1. A mixture of tin and aluminum as described in Example 2 was formed and added to the reactor. The reactor was purged with nitrogen, placed in a 400° C. temperature bath, and feed started to the reactor immediately. The molar ratio of hydrogen to trimethylchlorosilane was 2.8. Residence time of the reactants within the reactor was about 12.5 seconds. Product from the reactor was collected and analyzed as described in Example 1. The results are reported in Table 6.

TABLE 6

| | Tin Catalyzed Reaction of Trimethylchlorosilane With Hydrogen Gas and Aluminum | | | | | | | |
|---|---|---|---|---|---|---|---|---|
| | | Weight Percent Product Distribution | | | | | | |
| Run No. | % Si Conv. | $Me_2H_2$ | $Me_2H$ | MeH | $Me_3H$ | Me | $Me_2$ | $Me_3$ | $Me_4$ |
| 139 | 79.6 | 2.2 | 0.5 | 0.2 | 17.8 | 0.3 | 0.2 | 0.0 | 78.9 |

EXAMPLE 7

The tin catalyzed reaction of dimethyldichlorosilane with hydrogen gas and aluminum was evaluated at a reactor pressure of four atmospheres. The run was conducted in a reactor similar to that described in Example 1. A mixture of tin and aluminum as described in Example 2 was formed and added to the reactor. The reactor was purged with nitrogen and preheated in a 365° C temperature bath for nine minutes prior to start of feed of a dimethyldichlorosilane and hydrogen gas mixture. The molar feed ratio of hydrogen to dimethyldichlorosilane was 1.8 and the residence time was 49.8 seconds. The pressure of the reactor was four atm. Product from the reactor was collected and analyzed as described in Example 1. The results are reported in Table 7.

TABLE 7

| | Tin Catalyzed Reaction of Dimethyldichlorosilane With Hydrogen Gas and Aluminum at Four Atmospheres Pressure | | | | | | | |
|---|---|---|---|---|---|---|---|---|
| | | Weight Percent Product Distribution | | | | | | |
| Run No. | % Si Conv. | $Me_2H_2$ | $Me_2H$ | MeH | $Me_3H$ | Me | $Me_2$ | $Me_3$ | $Me_4$ |

| | | | | | | | | |
|---|---|---|---|---|---|---|---|---|
| 161 | 87.0 | 3.8 | 4.0 | 0.0 | 13.4 | 0.1 | 0.0 | 49.3 | 29.3 |

EXAMPLE 8

Two runs were conducted to evaluate the ability of a catalyst mixture comprising cuprous chloride, tin, and brass to catalyze the reaction of dimethyldichlorosilane with hydrogen gas and aluminum. The runs were conducted in a reactor similar to that described in Example 1. About 90 g of an aluminum and catalyst mixture comprising about 12 weight percent CuCl, 1800 ppm tin, and 3900 ppm brass was used in each run. The reactor was purged with nitrogen and preheated at the reaction temperature for 10 to 12 minutes. Run number 244 was conducted at a bath temperature of 325° C. For Run number 244, the molar feed ratio of hydrogen to dimethyldichlorosilane was 3.3 and the residence time of the reactants within the reactor was about 5.3 seconds. The reactor pressure was about one atm. Run number 251 was conducted at a bath temperature of 365° C. For Run number 251, the molar feed ratio of hydrogen to dimethyldichlorosilane was 3.6 and the residence time of the reactants within the reactor of about 5.2 seconds. The reactor pressure was about one atm. Product from each run was collected and analyzed as described in Example 1. The results are reported in Table 8.

TABLE 8

Catalytic Effect of Mixture Comprising Cuprous Chloride, Tin, and Brass on Reaction of Dimethyldichlorosilane With Hydrogen Gas and Aluminum

| Run No. | % Si Conv. | Weight Percent Product Distribution | | | | | | | |
|---|---|---|---|---|---|---|---|---|---|
| | | $Me_2H_2$ | $Me_2H$ | MeH | $Me_3H$ | Me | $Me_2$ | $Me_3$ | $Me_4$ |
| 244 | 65.8 | 0.26 | 16.6 | 0.0 | 0.5 | 0.0 | 0.0 | 82.1 | 0.6 |
| 251 | 80.2 | 1.37 | 16.7 | 0.0 | 1.9 | 0.9 | 0.0 | 76.8 | 1.8 |

EXAMPLE 9

A series of runs was conducted to evaluate the tin catalyzed reaction of dimethyldichlorosilane with gaseous hydrogen chloride and aluminum. The runs were conducted in a reactor similar to that described in Example 1. A mixture of tin and aluminum as described in Example 2 was formed and added to the reactor. The reactor was purged with nitrogen and placed in the temperature bath. Table 9a presents, for each run, the molar ratio of hydrogen chloride to dimethyldichlorisilane (H/Si), the residence time (Res., s), temperature of the temperature bath (Bath Temp., °C.) pressure within the reactor (Press., atm.), and the time of preheating of the catalyst and aluminum mixture (Preheat, Min.). In all cases where the catalyst and aluminum mixture were preheated, the preheating temperature was that at which the reaction was conducted.

TABLE 9a

| | | Process Parameters | | | |
|---|---|---|---|---|---|
| Run No. | H/Si | Res. (s) | Bath Temp. (°C.) | Press. (atm.) | Pre-Heat (Min.) |
| 126 | 0.94 | 8.97 | 262 | 1 | 0 |
| 128 | 3.13 | 4.56 | 240 | 1 | 0 |
| 168 | 1.52 | 9.54 | 300 | 1 | 10 |
| 170 | 3.18 | 7.65 | 365 | 1 | 8 |

For each run, product from the reactor was collected and analyzed as described in Example 1. The results are reported in Table 9b.

TABLE 9b

Tin Catalyzed Reaction of Dimethyldichlorosilane With Hydrogen Chloride Gas and Aluminum

| Run No. | % Si Conv. | Mole Percent Product Distribution | | | | | | | |
|---|---|---|---|---|---|---|---|---|---|
| | | $Me_2H_2$ | $Me_2H$ | MeH | $Me_3H$ | Me | $Me_2$ | $Me_3$ | $Me_4$ |
| 126 | 5.2 | 0.0 | 24.7 | 29.9 | 0.0 | 11.3 | 0.0 | 29.9 | 0.1 |
| 128 | 8.0 | 0.0 | 34.1 | 2.4 | 0.0 | 30.6 | 0.0 | 27.4 | 0.1 |
| 168 | 7.4 | 0.0 | 31.1 | 0.0 | 0.0 | 14.3 | 0.0 | 54.6 | 0.1 |
| 170 | 96.4 | 2.2 | 1.6 | 0.0 | 9.1 | 0.9 | 0.0 | 60.3 | 21.3 |

We claim:

1. A process for the hydrogenation of chlorosilanes, the process comprising contacting a chlorosilane described by formula $$R_aH_bSiCl_{4-a-b},$$

where each R is independently selected from a group consisting of alkyls comprising one to six carbon atoms, a=0, 1, 2, or 3; b=0, 1, 2, or 3; and a+b=0, 1, 2, or 3; with aluminum and a hydrogen source selected from a group consisting of hydrogen gas and gaseous hydrogen chloride in the presence of a catalyst selected from a group consisting of copper and copper compounds, tin and tin compounds, zinc and zinc compounds, and mixtures thereof, and recovering a hydrosilane resulting from the exchange of one or more of the chlorine atoms of the chlorosilane by hydrogen.

2. A process according to claim 1, where R is methyl.

3. A process according to claim 1, where the process is run as a continuous process in a fluidized-bed reactor.

4. A process according to claim 1, where the process is run as a continuous process in a packed-bed reactor.

5. A process according to claim 1, where the catalyst is Cu(I) chloride.

6. A process according to claim 1, where the catalyst comprises copper at a concentration of about 0.1 to 20 weight percent relative to the aluminum.

7. A process according to claim 1, where the catalyst comprises tin at a concentration of about 1500 ppm to 10,000 ppm relative to the aluminum.

8. A process according to claim 1, where the catalyst comprises tin at a concentration of about 3,000 ppm to 5,000 ppm relative to the aluminum.

9. A process according to claim 1, where the catalyst comprises zinc at a concentration of about 100 ppm to 10,000 ppm relative to the aluminum.

10. A process according to claim 1, where the catalyst is a mixture comprising CuCl, tin metal, and zinc metal.

11. A process according to claim 10, where the mixture is added to the process to provide a concentration relative to the aluminum of about 0.1 to 20 weight percent CuCl, 1 to 2000 ppm tin, and 100 to 10,000 ppm zinc.

12. A process according to claim 1, where the catalyst is a mixture comprising 10 to 15 weight percent CuCl, 1500 ppm to 2000 ppm tin, and 3500 ppm to 4200 ppm brass.

13. A process according to claim 1, where the hydrogen source provides at least one mole of hydrogen per mole of chlorosilane.

14. A process according to claim 1, where the process is conducted at a pressure of about one atm. to 100 atm.

15. A process according to claim 1, where the process is conducted at a pressure of about one atm to 15 atm.

16. A process according to claim 1, where the hydrogen source is hydrogen gas and the process is conducted at a temperature within a range of about 300° C. to 450° C.

17. A process according to claim 1, where the hydrogen source is hydrogen gas and the process is conducted at a temperature within a range of about 325° C. to 375° C.

18. A process according to claim 1, where the hydrogen source is hydrogen chloride and the process is conducted at a temperature within a range of about 250° C. to 450° C.

19. A process according to claim 1, where the hydrogen source is hydrogen chloride and the process is conducted at a temperature within a range of about 270° C. to 350° C.

20. A process according to claim 1, where a mixture comprising the aluminum and the catalyst is preheated.

21. A process according to claim 1, where the hydrosilane is dimethylchlorosilane.

22. A process according to claim 1, where the hydrosilane is trimethylsilane.

* * * * *